United States Patent [19]
Lindner et al.

[11] Patent Number: 6,117,817
[45] Date of Patent: Sep. 12, 2000

[54] ALGICIDE COMBINATION

[75] Inventors: Wolfgang Lindner; Jörg Rothermel, both of Seelze; Gerhard Wöhner, Garbsen; Erich Taschenbrecker, Wunstorf, all of Germany

[73] Assignee: Etc C.V., Hamilton, Bermuda

[21] Appl. No.: 08/860,894

[22] PCT Filed: Nov. 15, 1996

[86] PCT No.: PCT/EP96/05037

§ 371 Date: Sep. 24, 1998

§ 102(e) Date: Sep. 24, 1998

[87] PCT Pub. No.: WO97/18710

PCT Pub. Date: May 29, 1997

[30] Foreign Application Priority Data

Nov. 18, 1995 [DE] Germany .......................... 195 43 097

[51] Int. Cl.⁷ .......................... A01N 43/70; A01N 47/30
[52] U.S. Cl. .......................... 504/133; 504/155; 504/159
[58] Field of Search .......................... 504/133, 155, 504/159

[56] References Cited

FOREIGN PATENT DOCUMENTS

| 0 073 727 | 3/1983 | European Pat. Off. . |
| 26 53 652 | 6/1977 | Germany . |
| 2 074 448 | 11/1981 | United Kingdom . |

OTHER PUBLICATIONS

Derwent Abstract 92–128989/16 of JP 04–074104, Mar. 1992.

*Primary Examiner*—S. Mark Clardy
*Attorney, Agent, or Firm*—Robert F. Tavares

[57] ABSTRACT

The present invention relates to an algicide combination of triazine derivatives and N,N-dialkylurea derivatives and to its use for protecting industrial products against infestation and destruction by photoautotrope microorganisms.

22 Claims, No Drawings

ALGICIDE COMBINATION

This application is a 371 of PCT/EP96/05037 filed Nov. 15, 1996.

The present invention relates to an algicide combination of triazine derivatives and N,N-dialkylurea derivatives for preserving industrial materials. Industrial materials which are exposed to the weather and light are often rapidly colonized by bacteria, molds, yeasts, algae and lichen and adversely affected by their metabolic activities. In particular, coatings containing organic film formers on mineral substrates, textile finishes and wood paints and also materials made of plastics can be colonized relatively quickly by algae. Owing to this, some of these surfaces become discolored within a few months to an unsightly green/black. Additionally, algae prepare the ground for the growth of fungi, lichen and moss which can destroy the coating chemically or mechanically by their growth.

Especially the high-efficiency heat protection systems containing synthetic resin rendering which are nowadays mounted on exterior walls for energy conservation have, owing to their physical properties, a strong tendency to be infested by algae. To maintain their value, these coatings are therefore admixed with microbicides. Industrial materials which are in contact with water for a major part of their functional life are also easily colonized by algae. Examples include fishing nets and plastics used in swimming pools. The performance of fishing nets can be severely affected by growth of algae. It is therefore customary to apply coatings containing algicides. According to the prior art, ecologically unobjectionable tributyltin compounds are usually employed for this purpose.

Herbicides intended for use in crop protection are usually not suitable for finishing industrial materials, since they do not act against single-cell organisms, or they do not have the range of activity against algae and cyanobacteria required for the protection of materials. Furthermore, some of them are not stable to hydrolysis, such as, for example, sulfonylurea derivatives, or they cause discoloration of the industrial systems, such as, for example, dinitrophenol derivatives, or they are displaced too easily from the industrial materials under the influence of the weather, such as, for example linuron or chlorsulfuron.

There are therefore only very few crop protection agents which fulfill the requirements for use as algicide for finishing industrial materials. One example is the herbicide diuron, which is used in paints for exterior walls and in renders.

Triazine derivatives, such as, for example, 2-methylthio-4-cyclopropylamino-6-tert-butylamino-1,3,5-triazine (Mctt), are also used as algicides.

Additionally, there are fungicides which have an algistatic activity as a side effect. This category includes, for example, 3-iodopropynyl butylcarbamate, 2-n-octylisothiazolin-3-one and zinc pyrion. In modern coatings for exterior walls, combination products comprising fungicides and the abovementioned individual algicides have been used (for example DE-A 42 42 389). However, it has been observed in practice that the active compounds presently used do not have a sufficiently broad spectrum of activity against photoautotrope microorganisms, and that the desired long-term activity is often not achieved at low concentrations.

Thus, for example, significant discoloration caused by massive growth of algae was observed after only 2 years on the exterior wall of a high-efficiency heat protection system finished with 0.1% of diuron.

It is an object of the present invention to provide algicides having high long-term activity combined with a broad spectrum of activity against algae, cyanobacteria and other photoautotrope microorganisms which can be employed in industrial systems without adversely affecting their physicochemical properties, which are of low toxicity and which can advantageously be used for protection of the environment. Surprisingly, it has now been found that combinations of certain triazine derivatives and N,N-dialkylurea derivatives known per se exhibit a synergistically increased activity, i.e. they have a higher activity than the person skilled in the art would expect by adding the activities of the individual components. For example, it has been found that the combinations are active even against algae which have been isolated from exterior wall coatings finished in each case with the individual components. In other words, coatings which have been provided with such an active compound mixture are not colonized in regions where the finish with the individual algicides is ineffective.

The present invention, accordingly, provides an algicide combination which comprises at least one triazine derivative of the formula I

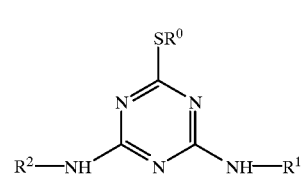

(I)

where
$R^0$ is methyl or ethyl,
$R^1$ and $R^2$ independently of one another are each alkyl, cycloalkyl, or alkoxyalkyl
and at least one N,N-dialkylurea derivative of the formula II

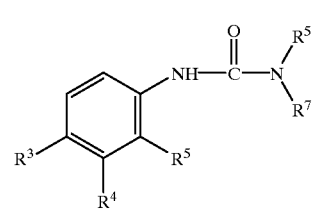

(II)

where
$R^3$ and $R^4$ independently of one another are each hydrogen, chlorine, bromine, alkyl, alkoxy, trifluoromethyl, aryloxy or substituted aryloxy,
$R^5$ is hydrogen, chlorine, bromine, fluorine or alkyl and
$R^6$ and $R^7$ independently of one another are each alkyl or alkoxy.

In the formulae I and II, alkyl groups may be branched or straight-chain and may be, for example, methyl, ethyl, n-propyl, i-propyl, n-butyl, i-butyl, sec-butyl, tert-butyl or pentyl. Preference is given to $(C_1-C_{10})$-alkyl groups, particular preference is given to $(C_1-C_4)$-alkyl groups. This applies correspondingly to alkoxy groups.

Cycloalkyl groups preferably have 3 to 8 carbon atoms, cyclopropyl being preferred. Aryloxy is preferably phenoxy. Substituted aryloxy is preferably phenoxy substituted by alkoxy, in particular by methoxy. $R^0$ is preferably methyl.

$R^1$ and $R^2$ independently of one another are each preferably methyl, ethyl, i-propyl, 1,2-dimethylpropyl, methoxypropyl, tert-butyl or cyclopropyl.

$R^3$ and $R^4$ independently of one another are each preferably hydrogen, chlorine, bromine, methyl, i-propyl, methoxy, trifluoromethyl, phenoxy or p-methoxyphenoxy.

$R^5$ is preferably hydrogen.

$R^6$ and $R^7$ independently of one another are each preferably methyl, methoxy or butyl.

Examples of particularly preferred compounds of the formula I are ametryn, desmetryn, dimethametryn, dipropetryn, methoprotryn, prometryn, terbutryn and 2-methylthio-4-cyclopropylamino-6-tert-butylamino-1,3,5-triazine (Mctt).

Examples of particularly preferred compounds of the formula II are chlorbromuron, chlortoluron, diuron, difenoxuron, fluometuron, isoproturon and neburon. Preferably the mixture includes no further algicides in addition to the compounds of the formulae I and II. Particular preference is given to algicide combinations according to the invention comprising 2-methylthio-4-cyclopropylamino-6-tert-butylamino-1,3,5-triazine and difenoxuron or diuron and to those comprising terbutryn and difenoxuron or diuron. The ratio of the compounds of the formulae I and II in the algicide combinations according to the invention is preferably between 10:1 and 1:10, particularly preferably between 4:1 and 1:4.

In particular, the algicide combinations according to the invention are present in the form of algicidally active preparations, formulations or other industrial systems, as specified further below. These comprise the algicide combinations generally in concentrations from 1 to 99% by weight, preferably from 5 to 50% by weight. The preparation of these formulations can be carried out for example by dissolving the compounds of the formulae I and II in a manner known per se.

The active compounds can be formulated as a solution in a manner known per se. The choice of solvent is not decisive, particularly suitable solvents for apolar systems are aromatic petroleum fractions, xylene, trimethylbenzene; ketones, such as, for example, acetone, cyclohexanone, isophorone, methyl isobutyl ketone; ethers and glycol ethers, such as, for example, diisopropyl ether, dimethoxyethane, diethylene glycol dimethyl ether, triethylene glycol dimethyl ether; esters, such as ethyl acetate, butyl acetate; glycols, mono- and diethers thereof or mono- or diesters thereof; amides, such as, for example, dimethylformamide, N-methylpyrrolidone and N-octylpyrrolidone. The mentioned solvents may also be employed as mixtures.

In solvent-free aqueous systems, preference is given to using water-based pastes of the algicides. The preparation of such pastes is known per se.

The compounds of the formulae I and II are known per se, and they can be prepared by methods known from the literature, or purchased commercially.

The algicide combinations according to the invention exhibit a high activity and a broad spectrum of activity against algae, cyanobacteria and other photoautotrope microorganisms, and they can be used for protecting industrial products against infestation and destruction by such microorganisms. Examples include green algae of the species Chlamydomonas, Chlorella, Chlorococcum, Microspora, Platymonas, Pleurococcus, Scenedesmus, Stichococcus, Trentepohlia and Ulothrix, blue-green algae (cyanophytes) such as Anabaena, Anacystis, Chroococcus, Gleocapsa, Mycrocystis, Nostoc, Oscillatoria, Scytonema and Spirulina, and yellow-green algae such as Tribonema.

Owing to their high alkali resistance and low water-solubility, the high activity and the broad spectrum of activity is particularly advantageous in materials such as paints for exterior walls, synthetic resin rendering, wood coatings, wood varnishes, coatings for concrete, roof tile coatings, silicate paints, sealing materials, textile finishes and other industrial systems over long periods of time. In these areas of application, the advantages are therefore particularly pronounced in comparison to the individual components.

The algicide combinations according to the invention can also be employed in the form of polyvinyl chloride-containing plastics, since they are temperature-stable and will not be destroyed by the thermal stress occurring during calendering.

The use in compositions for coating fishing nets is also advantageous, since the combination products can be prepared in easily processible formulations and in particular as a finely divided aqueous dispersion.

The use concentration depends on the kind of material to be protected, the leach out stress and the expected degree of infestation by microbes and is from 0.005 to 3% by weight, preferably from 0.01 to 0.2% by weight, of algicide combination, based on the material to be protected.

The algicide combinations according to the invention can also be employed in combination with other known antimicrobial substances. Examples include the following fungicides and bactericides:

Benzimidazole derivatives, such as, for example, carbendazim or thiabendazole, quaternary ammonium salts (quats), such as, for example, didecyldimethylammonium chloride, thiocyanate compounds, such as, for example, 2-thiocyanatomethylthiobenzothiazole, carbamates, such as, for example, iodopropynyl butylcarbamate, isothiazolinone derivatives, such as, for example, 2-octylisothiazolin-3-one, triazole fungicides, such as, for example, tebuconazole, imidazole fungicides, such as, for example, prochloraz, halogenated sulfides, such as, for example, dichlofluanid, tolylfluanid, captan, folpet and nitriles, such as, for example, tetrachlorophthalodinitrile.

Formulations comprising an algicide combination according to the invention and a fungicide mixture are particularly advantageous. A preferred example is a combination of carbendazim, 2-octylisothiazolinone, terbutryn and difenoxuron. These active compound combinations ensure a comprehensive long-term protection of industrial materials against infestation by discolorizing and destructive microorganisms.

EXAMPLE 1

The activity of the algicide combinations according to the invention against algae is measured by determining the minimum inhibitory concentrations (MIC values). (Literature: K. Grossmann, R. Berghaus, G. Retzlaff; Pesticide Science (1992), 35, 283).

In each case, a stock solution of 2-methylthio-4-cyclopropylamino-6-tert-butylamino-1,3,5-triazine (Mctt) and diuron is prepared. For this purpose, in each case about 1000 mg of the active compound are dissolved in 100 ml of ethanol.

In a volumetric flask, ethanol is added to 1.0 ml of the solution to make up 100 ml. Concentration of the stock solutions: about 100 mg/l.

From these stock solutions, a series of dilutions in ethanol of both the individual active compounds and the combinations is prepared in the ratios stated in the table using 24-well microtiter plates (Nunclon from Nunc). The solvent is evaporated in a stream of air. 1 ml of a dilute suspension of algae is then pipetted into each of the microtiter plate wells. Additionally, an algae suspension free of active compound is added as a control to each of the microtiter plates. The test organism used is an algae strain isolated from a high-efficiency heat protection system whose final coating had been finished with a commercial film preservative based on 2-methylthio-4-cyclopropylamino-6-tert-butylamino-1,3,5-triazine (Mctt). The algae culture, which had been grown under sterile conditions, is diluted with a sterile Bold growth medium in such a way that a very weak green color remains. The microtiter plates are then incubated under continuous irradiation with a daylight lamp at 21° C. for 7 days. After 7 days, the control wells free of active compound are colonized to a considerable extent. The growth of algae in each well is compared with the control wells and assessed by the following scheme:

- no growth of algae
+ as green as the control solutions
(+) a lighter green than the control solutions, but noticeable growth of algae The synergistic increase in activity is calculated by the method of Kull (Applied Microbiology Vol. 9, p. 538–41 (1961):

$$\text{Synergism} = \frac{QA}{Qa} + \frac{QB}{Qb}$$

QA=MIC value of Mctt as concentration in the combination
Qa=MIC value of Mctt as individual component
QB=MIC value of diuron as concentration in the combination
Qb=MIC value of diuron as individual component A value <1 in the formula above indicates a synergistic increase in activity.

TABLE

| No. | MIC value sum of the act. comps. mg/l | MIC value MCtt mg/l | MIC value diuron mg/l | Synergism by the method of Kull | Mass ratio Mctt/diuron |
|---|---|---|---|---|---|
| 1 | 0.039 | 0.031 | 0.008 | 0.49 | 3.9 |
| 2 | 0.039 | 0.023 | 0.016 | 0.54 | 1.4 |
| 3 | 0.039 | 0.016 | 0.023 | 0.58 | 0.7 |
| 4 | 0.039 | 0.008 | 0.031 | 0.62 | 0.25 |
| 5 | 0.088 | 0.088 | — | | Comparison, pure act. compd. |
| 6 | 0.058 | — | 0.058 | | Comparison, pure act. compd. |

EXAMPLE 2

The method of Example 1 was used, but terbutryn was employed instead of Mctt

TABLE

| No. | MIC value sum of the act. comps. mg/l | MIC value terbut. mg/l | MIC value diuron mg/l | Synergism by the method of Kull | Mass ratio terbut/diuron |
|---|---|---|---|---|---|
| 1 | 0.058 | 0.046 | 0.012 | 0.73 | 3.8 |
| 2 | 0.058 | 0.035 | 0.025 | 0.83 | 1.4 |

TABLE-continued

| No. | MIC value sum of the act. comps. mg/l | MIC value terbut. mg/l | MIC value diuron mg/l | Synergism by the method of Kull | Mass ratio terbut/diuron |
|---|---|---|---|---|---|
| 3 | 0.039 | 0.016 | 0.023 | 0.58 | 0.7 |
| 4 | 0.039 | 0.008 | 0.031 | 0.63 | 0.25 |
| 5 | 0.088 | 0.088 | — | | Comparison, pure act. compd. |
| 6 | 0.058 | — | 0.058 | | Comparison, pure act. compd. |

EXAMPLE 3

Example of the Preparation of an Algicide Combination 40 kg of carboxymethylcellulose were stirred with 1460 l of water in a dissolver until the cellulose is swollen up completely. 80 kg of diuron (4%) and 320 kg of terbutryn (16%) and 100 kg of kaolin are admixed and the dispersion is bead-milled to a particle size of below 10 micrometer.

This homogeneous paste can be incorporated without any problems into water-based paints and plastering for exterior walls without negatively affecting their physical properties.

EXAMPLE 4

Test for the Algistatic Preservation of Films 0.025% of finely powdered difenoxuron and 0.025% of finely ground Mctt were incorporated into a microbicide-free commercial paint for exterior walls based on a dispersion of styrene acrylate. For comparison, samples of similar prior-art paints were finished with in each case 0.025% and 0.05% of difenoxuron or Mctt (abbreviated as difenox in the table below).

The resulting samples of paint were applied to round filter papers (No. 597, Schleicher & Schull, diameter 5.5 cm) at 300 g/m$^2$ in each case and then dried at a temperature of 30° C. for 72 hours. To simulate leaching by rain, the painted test materials were watered with tap water for 96 hours. The leach water was changed every 24 hours.

The test of the resistance against colonization by algae was carried out on solid Bold-algae growth media. After the dry test materials had been sterilized on both sides, they were placed in Petri dishes onto the growth media under UV light. For each test, 5 ml of a well developed algae culture in Bold growth medium was applied under sterile conditions to the surface to be tested in such a way that the paint surface was colored light green.

After an incubation time of 14 days at a temperature of 29° C., the degree of algae growth on the paints was determined visually using a scale of 0 to 4:

0 paint not colonized
1 paint slightly colonized, less than 10% of the surface
2 paint colonized, 10 to 30% of the surface
3 paint colonized, 30 to 60% of the surface
4 paint overgrown, more than 60% of the surface.

The results are shown in the table below.

TABLE

Test for the algistatic preservation of films

| Algicide | Conc. | Colonization by *Chlorella fusca* | |
|---|---|---|---|
| Difenox.-Mctt 1:1 | 0.05% (0.025 +0.025%) | 0 | |
| Mctt | 0.05% | 0 | Comparison |
| Mctt | 0.025% | 1 | Comparison |
| Difenox. | 0.05% | 2 | Comparison |
| Difenox. | 0.025% | 2 | Comparison |

What is claimed is:

1. An algicide combination which comprises at least one triazine derivative of the formula I

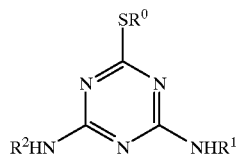

where
R⁰ is methyl or ethyl,
R¹ and R² independently of one another are each alkyl, cycloalkyl, or alkoxyalkyl
and at least one N,N-dialkylurea derivative of the formula II

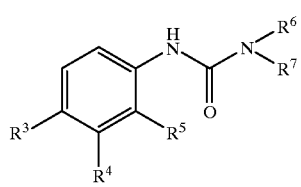

where
R³ and R⁴ independently of one another are each hydrogen, chlorine, bromine, alkyl, alkoxy, trifluoromethyl, aryloxy or substituted aryloxy,
R⁵ is hydrogen, chlorine, bromine, fluorine or alkyl and
R⁶ and R⁷ independently of one another are each alkyl or alkoxy, provided that when R¹ is ethyl and R² is tertiary butyl, neither R⁶ nor R⁷ is methoxy or n-butyl.

2. An algicide combination as claimed in claim 1, wherein R⁰ is methyl,
R¹ and R² are methyl, ethyl, i-propyl, 1,2-dimethylpropyl, methoxypropyl, tertiary butyl or cyclopropyl,
R³ and R⁴ are hydrogen, chlorine, bromine, methyl, i-propyl, methoxy, trifluoromethyl, phenoxy or p-methoxyphenoxy,
R⁵ is hydrogen, and
R⁶ and R⁷ are methoxy, methyl or butyl.

3. The combination of claim 2 wherein R¹ is tertiary butyl, R² is ethyl or cyclopropyl, R³ is p-methoxyphenoxy or chlorine, R⁴ is chlorine or hydrogen, R⁶ is methyl and R⁷ is methyl, methoxy or butyl.

4. The combination of claim 3 wherein the triazine derivative and the N,N-dialkylurea derivative are present in a proportion of from about 1 part triazine to about 10 parts urea to about 10 parts triazine to about 1 part urea.

5. The combination of claim 4 wherein the triazine is 2-methylthio-4-cyclopropylamino-6-tert-butylamino-1,3,5-triazine (Irgarol) and the urea is N'-(3,4-dichlorophenyl)-N,N-dimethylurea (Diuron).

6. The combination of claim 4 wherein the triazine is 2-methylthio-4-cyclopropylamino-6-tert-butylamino-1,3,5-triazine (Irgarol) and the urea is 3-[4-(methoxyphenoxy)phenyl]-1,1-dimethylurea (Difenoxuron).

7. The combination of claim 4 wherein the triazine is 2-methylthio-4-ethylamino-6-tert-butylamino-1,3,5-triazine (Terbutryn) and the urea is N'-(3,4-dichlorophenyl)-N,N-dimethylurea (Diuron).

8. The combination of claim 4 wherein the triazine is 2-methylthio-4-ethylamino-6-tert-butylamino-1,3,5-triazine (Terbutryn) and the urea is 3-[4-(methoxyphenoxy)phenyl]-1,1-dimethylurea (Difenoxuron).

9. A coating composition containing an effective amount of an algicide combination which comprises at least one triazine derivative of the formula I

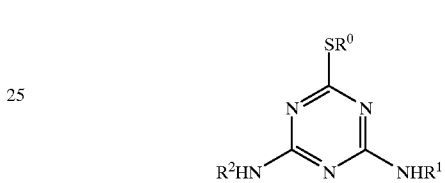

where
R⁰ is methyl,
R¹ and R² independently of one another are each methyl, ethyl, i-propyl, 1,2-dimethylpropyl, methoxypropyl, tertiary butyl or cyclopropyl,
and at least one N,N-dialkylurea derivative of the formula II

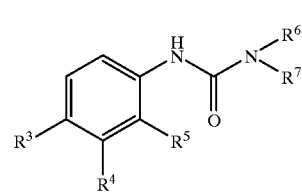

where
R³ and R⁴ independently of one another are each hydrogen, chlorine, bromine, methyl, i-propyl, methoxy, trifluoromethyl, phenoxy or p-methoxyphenoxy,
R⁵ is hydrogen,
R⁶ and R⁷ independently of one another are each methoxy, methyl or butyl, provided that when R¹ is ethyl and R² is tertiary butyl, neither R⁶ nor R⁷ is methoxy or n-butyl.

10. The composition of claim 9 wherein R¹ is tertiary butyl, R² is ethyl or cyclopropyl, R³ is p-methoxyphenoxy or chlorine, R⁴ is chlorine or hydrogen, R⁶ is methyl and R⁷ is methyl, methoxy or butyl.

11. The composition of claim 10 wherein the triazine derivative and the N,N-dialkylurea derivative are present in a proportion of from about 1 part triazine to about 10 parts urea to about 10 parts triazine to about 1 part urea.

12. The composition of claim 11 wherein the triazine is 2-methylthio-4-cyclopropylamino-6-tert-butylamino-1,3,5- triazine (Irgarol) and the urea is N'-(3,4-dichlorophenyl)-N,N-dimethylurea (Diuron).

13. The composition of claim 11 wherein the triazine is 2-methylthio-4-cyclopropylamino-6-tert-butylamino-1,3,5-triazine (Irgarol) and the urea is 3-[4-(methoxyphenoxy)phenyl]-1,1-dimethylurea (Difenoxuron).

14. The composition of claim 11 wherein the triazine is 2-methylthio-4-ethylamino-6-tert-butylamino-1,3,5-triazine (Terbutryn) and the urea is N'-(3,4-dichlorophenyl)-N,N-dimethylurea (Diuron).

15. The composition of claim 11 wherein the triazine is 2-methylthio-4-ethylamino-6-tert-butylamino-1,3,5-triazine (Terbutryn) and the urea is 3-[4-(methoxyphenoxy)phenyl]-1,1-dimethylurea (Difenoxuron).

16. A method for protecting an industrial product against infestation and destruction by algae, cyanobacteria and other photoautotrope microorganisms which comprises incorporating in said industrial product an effective amount of an algicide combination which comprises at least one triazine derivative of the formula I

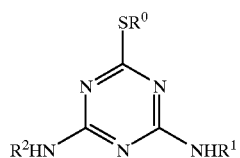

where

R⁰ is methyl,

R¹ and R² independently of one another are each methyl, ethyl, i-propyl, 1,2-dimethylpropyl, methoxypropyl, tertiary butyl or cyclopropyl, and at least one N,N-dialkylurea derivative of the formula II

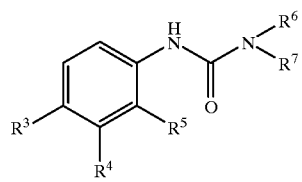

where

R³ and R⁴ independently of one another are each hydrogen, chlorine, bromine, methyl, i-propyl, methoxy, trifluoromethyl, phenoxy or p-methoxyphenoxy, R⁵ is hydrogen, R⁶ and R⁷ independently of one another are each methoxy, methyl or butyl, provided that when R¹ is ethyl and R² is tertiary butyl, neither R⁶ nor R⁷ is methoxy or n-butyl.

17. The method of claim 16 wherein R¹ is tertiary butyl, R² is ethyl or cyclopropyl, R³ is p-methoxyphenoxy or chlorine, R⁴ is chlorine or hydrogen, R⁶ is methyl and R⁷ is methyl, methoxy or butyl.

18. The method of claim 17 wherein the triazine derivative and the N,N-dialkylurea derivative are present in a proportion of from about 1 part triazine to about 10 parts urea to about 10 parts triazine to about 1 part urea.

19. The method of claim 18 wherein the triazine is 2-methylthio-4-cyclopropylamino-6-tert-butylamino-1,3,5-triazine (Irgarol) and the urea is N'-(3,4-dichlorophenyl)-N,N-dimethylurea (Diuron).

20. The method of claim 19 wherein the triazine is 2-methylthio-4-cyclopropylamino-6-tert-butylamino-1,3,5-triazine (Irgarol) and the urea is 3-[4-(methoxyphenoxy)phenyl]-1,1-dimethylurea (Difenoxuron).

21. The method of claim 20 wherein the triazine is 2-methylthio-4-ethylamino-6-tert-butylamino-1,3,5-triazine (Terbutryn) and the urea is N'-(3,4-dichlorophenyl)-N,N-dimethylurea (Diuron).

22. The method of claim 21 wherein the triazine is 2-methylthio-4-ethylamino-6-tert-butylamino-1,3,5-triazine (Terbutryn) and the urea is 3-[4-(methoxyphenoxy)phenyl]-1,1-dimethylurea (Difenoxuron).

* * * * *